United States Patent
Endo et al.

(10) Patent No.: US 10,241,064 B2
(45) Date of Patent: Mar. 26, 2019

(54) NUCLEAR MAGNETIC RESONANCE MEASUREMENT APPARATUS HAVING AN EXHAUST GAS PROCESSING MECHANISM AND METHOD FOR PROCESSING EXHAUST GAS IN A NUCLEAR MAGNETIC RESONANCE MEASUREMENT APPARATUS

(71) Applicant: JEOL Ltd., Tokyo (JP)

(72) Inventors: Yuki Endo, Tokyo (JP); Masahide Nishiyama, Tokyo (JP)

(73) Assignee: JEOL Ltd., Tokyo (JP)

( * ) Notice: Subject to any disclaimer, the term of this patent is extended or adjusted under 35 U.S.C. 154(b) by 167 days.

(21) Appl. No.: 15/384,356

(22) Filed: Dec. 20, 2016

(65) Prior Publication Data

US 2017/0176362 A1 Jun. 22, 2017

(30) Foreign Application Priority Data

Dec. 21, 2015 (JP) .................................. 2015-248842

(51) Int. Cl.
    *G01N 24/08*     (2006.01)
    *G01R 33/31*     (2006.01)

(52) U.S. Cl.
    CPC ........... *G01N 24/082* (2013.01); *G01R 33/31* (2013.01)

(58) Field of Classification Search
    CPC .............................. G01N 24/082; G01R 33/31
    See application file for complete search history.

(56) References Cited

U.S. PATENT DOCUMENTS

| | | | | |
|---|---|---|---|---|
| 3,525,928 A * | 8/1970 | Nagao | .................... | G01R 33/30 165/109.1 |
| 3,987,361 A * | 10/1976 | Martin, Jr. | ............. | G01N 33/26 324/315 |
| 4,275,350 A * | 6/1981 | Hill | ...................... | G01R 33/307 324/321 |
| 4,587,492 A * | 5/1986 | Laudermilch | .......... | G01R 33/31 324/318 |
| 4,940,942 A * | 7/1990 | Bartuska | ................ | G01R 33/31 324/307 |
| 5,289,130 A * | 2/1994 | Doty | .................... | G01R 33/307 324/307 |
| 2003/0102867 A1 | 6/2003 | Hioka | | |
| 2014/0055138 A1* | 2/2014 | Takegoshi | .......... | G01R 33/3403 324/322 |

FOREIGN PATENT DOCUMENTS

| | | |
|---|---|---|
| JP | 4504308 A | 7/1992 |
| JP | 200081472 A | 3/2000 |
| JP | 2003177172 A | 6/2003 |
| JP | 2004212354 A | 7/2004 |

* cited by examiner

*Primary Examiner* — G. M. A Hyder
(74) *Attorney, Agent, or Firm* — The Webb Law Firm

(57) ABSTRACT

A probe head in a nuclear magnetic resonance measurement apparatus includes a rotating mechanism. In the probe head, an exhaust gas having a high temperature or a low temperature is discharged from a discharge port of the rotating mechanism. An additive gas having room temperature is introduced into the probe head through a plurality of ejection holes. The additive gas is mixed with the exhaust gas, and, as a result, an exhaust gas mixture having a temperature closer to room temperature than is the temperature of the sample is produced. A deflector regulates the direction in which the exhaust gas flows.

14 Claims, 7 Drawing Sheets

NUCLEAR MAGNETIC RESONANCE MEASUREMENT APPARATUS HAVING AN EXHAUST GAS PROCESSING MECHANISM AND METHOD FOR PROCESSING EXHAUST GAS IN A NUCLEAR MAGNETIC RESONANCE MEASUREMENT APPARATUS

CROSS REFERENCE TO RELATED APPLICATION

The entire disclosure of Japanese Patent Application No. 2015-248842 filed on Dec. 21, 2015 including the specification, claims, drawings, and abstract is, incorporated herein by reference in its entirety.

TECHNICAL FIELD

The present invention relates to a nuclear magnetic resonance measurement apparatus, and, in particular, relates to processing of an exhaust gas.

BACKGROUND

Nuclear magnetic resonance (NMR) measurement apparatuses measure nuclear magnetic resonance that occurs in a solid, liquid, or gaseous sample. During the nuclear magnetic resonance measurement, a temperature control gas is used to adjust the temperature of the sample to a predetermined temperature (for example, a high temperature or a low temperature). Specifically, the gas is supplied to a periphery of a sample tube in which a sample is placed, and the temperature of the sample is controlled to a predetermined temperature through heat exchange between the gas and the sample tube.

By varying the temperature of the gas, the temperature of the sample can be adjusted to a desired temperature or a set temperature. Gases used in this manner are referred to as, for example, "sample gas," "sample temperature varying gas," "sample temperature control gas," or "variable temperature (VT) gas." In the following description, such gases are referred to as "VT gas."

JP 4-504308 A, JP 2000-81472 A, and JP 2003-177172 A disclose nuclear magnetic resonance measurement apparatuses that measure solid samples. In such a nuclear magnetic resonance measurement apparatus, a rotating mechanism (a spinner) drives a sample tube in which a sample is placed, to rotate while the sample tube is being tilted at a predetermined angle. The rotating mechanisms disclosed in JP 4-504308 A and JP 2003-177172 A include a VT gas supply path, a sample chamber, and a VT gas discharge path. The sample chamber houses a detection coil and a sample portion of the sample tube. A VT gas is introduced into the sample chamber, and the temperature of the sample is controlled based on the temperature of the VT gas. JP 2004-212354 A discloses a nuclear magnetic resonance measurement apparatus that measures a gaseous or liquid sample. In this apparatus, a VT gas is similarly supplied to a periphery of a sample tube in which a sample is placed.

SUMMARY

Technical Problem

A VT gas discharged from the rotating mechanism is released into a space in a probe head, and then is exhausted to the outside via an upper opening of the probe head and an exhaust pipe that is in communication with the upper opening of the probe head. The temperature of the VT gas ranges, for example, between −35° C. and +120° C. In other words, the temperature of the VT gas may be significantly lower or significantly higher than room temperature. If a hot VT gas (an exhaust gas) is discharged from the rotating mechanism, the exhaust gas elevates the temperature of structural elements that are located in a periphery of the rotating mechanism or downstream of the rotating mechanism. The elevated temperature deteriorates or damages, for example, shim coils, O rings, adhesives, or other components. On the other hand, if a cold exhaust gas cools structural elements that are located in a periphery of the rotating mechanism or downstream of the rotating mechanism, freezing or condensation occurs on the surfaces of those structural elements. This deteriorates the electrical characteristics of the probe.

These problems cause a constraint in that the temperature variable range of the VT gas cannot be broadened easily. Another problem is the necessity to incorporate a special thermal insulation structure in order to avoid the above-described problems. The above-described problems may be observed in any nuclear magnetic resonance measurement apparatus that produces a high-temperature or low-temperature exhaust gas.

The present invention is directed toward moderating or eliminating thermal influence of an exhaust gas that is produced after a gas is used for controlling a sample temperature. The present invention is directed toward providing a new method for thermally processing an exhaust gas that is produced in a nuclear magnetic resonance measurement apparatus.

Solution to Problem

According to one aspect of the present invention, there is provided a nuclear magnetic resonance measurement apparatus comprising a structure body having a sample space, the space being configured to house a sample that is to be measured by nuclear magnetic resonance, into which a sample gas for adjusting a temperature of the sample to a predetermined temperature is introduced; and an exhaust gas processing mechanism configured to mix an additive gas with an exhaust gas that is the sample gas exiting from the sample space, to generate an exhaust gas mixture having a temperature that is closer to room temperature than is the predetermined temperature.

In the above-described configuration, the additive gas for controlling the temperature of the exhaust gas is mixed with the exhaust gas exiting from the sample space, to generate an exhaust gas mixture having a temperature that is closer to room temperature than is the temperature of the exhaust gas. The exhaust gas mixture is exhausted. For example, if the exhaust gas has a high temperature, an additive gas of room temperature or having a temperature that is lower than room temperature is mixed with the high-temperature exhaust gas. On the other hand, if the exhaust gas has a low temperature, an additive gas of room temperature or having a temperature that is higher than room temperature is mixed with the low-temperature exhaust gas. The temperature of the exhaust gas is regulated by such a simple method based on the mixing of the gases. A compressed gas of room temperature that is produced by, for example, a compressor may be used as the additive gas.

In an embodiment, the above-described structure body is a rotating mechanism that is used in measurements of solid samples. However, the above-described configuration may be generally applied to nuclear magnetic resonance measurement apparatuses in which a sample gas is used. For example, the above-described configuration may also be applied to nuclear magnetic resonance measurement apparatuses that measure liquid or gaseous samples. In that case, the above-described structure body is, for example, a tubular component for housing a sample tube. Although it is preferred that the mixing of the gases is performed outside the structure body, the mixing of the gases may be performed within the structure body in a discharge path extending from a sample chamber to a discharge opening. When the mixing of the gases is performed outside the structure body, the mixing of the gases may be performed within a probe head that houses the structure body. Alternatively, the mixing of the gases may be performed in an exhaust pipe that is in communication with the probe head. To avoid excessive heating or cooling of structural elements that are located within or outside the probe, the mixing of the gases may be performed near an exhaust outlet of the structure body.

In an embodiment, the above-described exhaust gas processing mechanism includes, for example, an additive gas generator and an additive gas supply system. The supply system may be composed of, for example, an additive gas pipe and a plurality of additive gas ejection holes. As the additive gas is intended to control the temperature of the exhaust, the additive gas is fed at a flow rate that is substantially equal to the flow rate of the sample gas or that is suitable for the purpose of moderating the temperature. In this context, the additive gas is distinct from a bearing gas that is supplied to air bearings in the rotating mechanism, or a drive gas that is blown against a turbine of the sample tube in the rotating mechanism. In an embodiment, the additive gas is supplied via a dedicated pipe (a flow path) to, or near, structural elements, and the flow rate of the additive gas is set or controlled independently.

In an embodiment, the nuclear magnetic resonance measurement apparatus includes a hollow component that houses the structure body, the structure body has a discharge port configured to discharge the exhaust gas into the hollow component, and in the hollow component, the additive gas is mixed with the exhaust gas discharged through the discharge port.

The above-described hollow component may be, for example, a probe container, or may consist of a probe container and an exhaust pipe. In typical cases, the hollow component is a probe container. In that case, the mixing of the gases is performed in the probe container. When the hollow component consists of a probe container and an exhaust pipe, the mixing of the gases may be performed in the exhaust pipe. The hollow component may consist of a probe container and an exhaust pipe when the outlet of the exhaust port (the exhaust outlet) extends to near the inlet of the exhaust pipe or extends into the inside of the exhaust pipe.

In an embodiment, the hollow component is a container of a nuclear magnetic resonance measurement probe, and the structure body is a rotating mechanism configured to rotate a sample tube in which the sample is placed. In an embodiment, a first pipe configured to feed the sample gas and a second pipe configured to feed a gas for rotating the sample tube are connected to the rotating mechanism, and the exhaust gas processing mechanism includes a third pipe configured to feed the additive gas into the container, the third pipe being different from the first pipe and the second pipe. The concept of the gas for rotating the sample tube encompasses both a bearing gas and a drive gas as described above. The third pipe may be inserted into a bore through an upper opening of the bore, or the third pipe may be formed in the probe.

In an embodiment, the exhaust gas processing mechanism includes at least one ejection hole that is in communication with the third pipe, the at least one ejection hole being configured to eject the additive gas into the container. A path of circulation (forced convection) of the additive gas may be formed in the container so as to prevent the additive gas from colliding against the exhaust gas and staying in the same place (so as to prevent the two flows from colliding completely head-on against each other) in the container.

In an embodiment, the exhaust gas processing mechanism includes a plurality of ejection holes configured to eject the additive gas toward a periphery of the rotating mechanism. In this configuration, the direction in which the additive gas is ejected can be determined such that the additive gas will not go straight toward the discharge port. In an embodiment, jets of the additive gas first go down along the inner surface of the container, and then is bounced back by the bottom surface and rise up so as to surround the rotating mechanism. The positions and the orientation of the plurality of ejection holes may be determined and a separation component configured to assist the flow may be disposed so as to form such a flow path of the additive gas.

In an embodiment, in the container, a flow of the additive gas extending from the plurality of ejection holes merges with a flow of the exhaust gas extending from the discharge port. The flow of the exhaust gas and the flow of the additive gas may be aligned in the same direction at a location where they merge or meet with each other, to prevent these flows from colliding with each other.

In an embodiment, a deflector is disposed in the hollow component, and the exhaust gas exiting through the discharge port is guided by the deflector toward an exhaust outlet. The deflector is a component that is different from the container, and is a component for controlling the flow of the exhaust gas (and the additive gas). For example, when the discharge port faces toward a corner portion of the container, the exhaust gas directly impinges upon the corner portion to cause this portion to become hot (or cold). A deflector may be disposed in front of the corner portion to control the direction of the flow of the exhaust gas (preferably, to direct the exhaust gas toward the exhaust pipe) to prevent the exhaust gas from directly reaching the corner portion.

In an embodiment, a flow of the exhaust gas and a flow of the additive gas are separated by the deflector. In this configuration, the flow of the exhaust gas is formed by a first surface of the deflector, and the flow of the additive gas is formed by a second surface of the deflector.

In an embodiment, the deflector has a surface that faces toward the discharge port, the surface being a concave curved surface. In this configuration, the exhaust gas can be captured and directed effectively.

In an embodiment, the structure body has an exhaust port that projects in a direction toward which the exhaust gas mixture flows, and an end of the exhaust port is the discharge port. In this configuration, the direction in which the exhaust gas is exhausted can be defined directly.

In an embodiment, the nuclear magnetic resonance measurement apparatus includes a pipe structure connected to the container, and the pipe structure includes a first flow path in which the exhaust gas mixture flows; a second flow path in which the additive gas flows; and a third flow path in which a shield gas flows, the third flow path being disposed between the first flow path and the second flow path to prevent or reduce heat exchange between the exhaust gas mixture and the additive gas. As the shield gas can retard the heat exchange or heat conduction between the exhaust gas mixture and the additive gas, the function of the additive gas can be fully obtained. A thermal insulation structure (a vacuum layer) or a thermal insulation component may be disposed rather than the third flow path.

In an embodiment, the pipe structure includes a shield gas ejection hole configured to feed the shield gas into the first flow path toward the downstream side of the first flow path. In this configuration, as the velocity of the flow of the exhaust gas mixture in the first flow path is increased and the atmospheric pressure on the side closer to the probe is lowered, the exhaust of the exhaust gas mixture can be promoted.

According to another aspect of the present invention, there is provided a method for processing an exhaust gas in a nuclear magnetic resonance measurement apparatus, the method comprising introducing a sample gas for heating or cooling a sample that is to be measured by nuclear magnetic resonance, into a sample space that houses the sample, to adjust a temperature of the sample to a predetermined temperature; mixing an additive gas with an exhaust gas that is the sample gas exiting from the sample space, to generate an exhaust gas mixture having a temperature that is closer to room temperature than is the predetermined temperature; and exhausting the exhaust gas mixture.

This method is implemented in a nuclear magnetic resonance measurement apparatus. An exhaust gas processing mechanism may be added to an existing nuclear magnetic resonance measurement apparatus (that is, a nuclear magnetic resonance measurement apparatus that is already installed and in operation).

BRIEF DESCRIPTION OF DRAWINGS

Embodiments of the present disclosure will be described by reference to the following figures, wherein.

DESCRIPTION OF EMBODIMENTS

Embodiments of the present invention will be described below with reference to the drawings.

Figure 1:
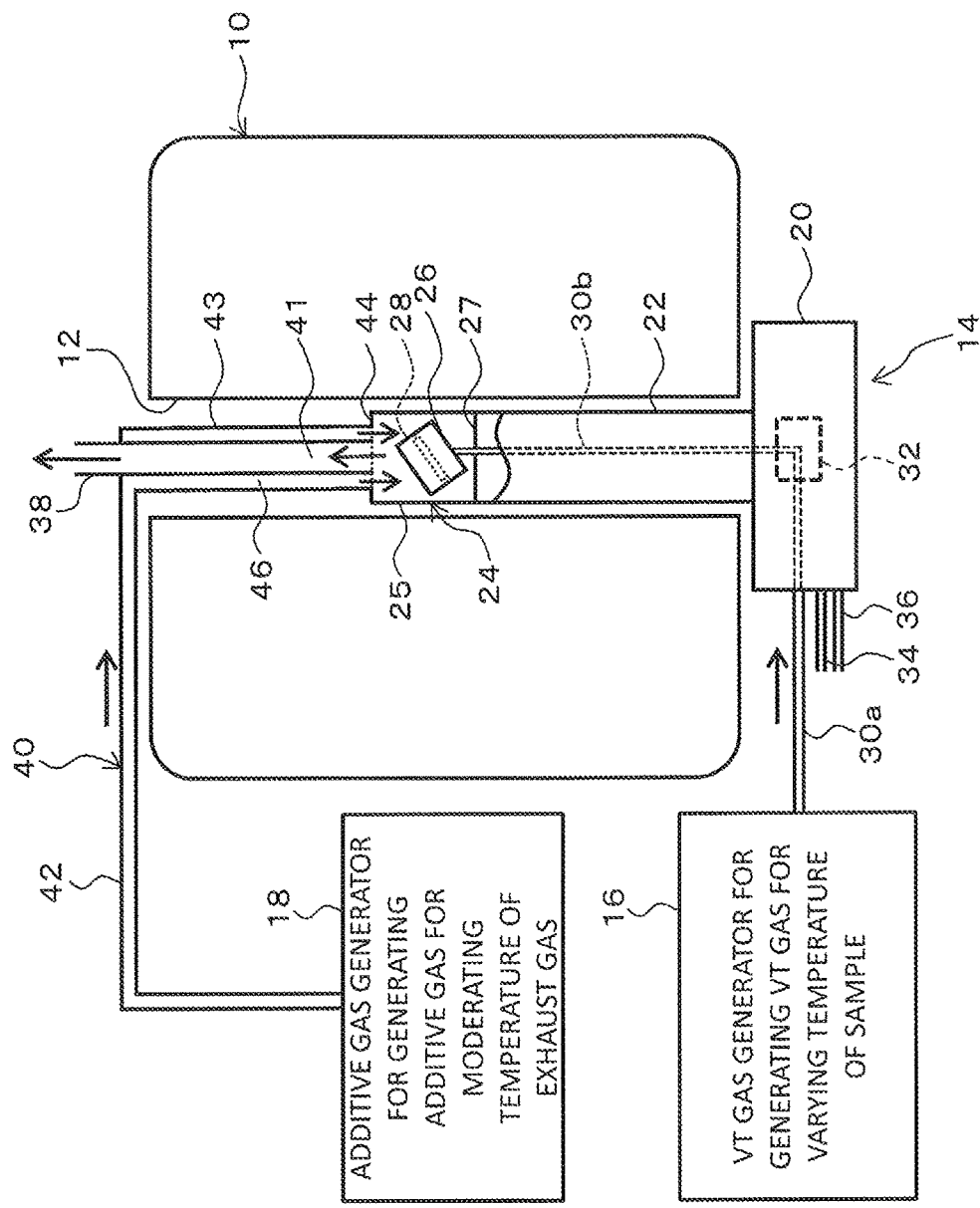
FIG. 1 illustrates a nuclear magnetic resonance measurement apparatus according to an embodiment of the present invention.

FIG. 1 illustrates a nuclear magnetic resonance (NMR) measurement apparatus according to an embodiment of the present invention. The illustrated NMR measurement apparatus measures nuclear magnetic resonance that occurs in a solid sample.

In FIG. 1, the NMR measurement apparatus is illustrated in a simplified or schematic manner. The NMR measurement apparatus includes, for example, a static magnetic field generator 10, an NMR measurement probe (an NMR probe) 14, a VT gas generator 16 for generating a VT gas for varying the temperature of a sample, an additive gas generator 18 for generating an additive gas for moderating the temperature of an exhaust gas, and an additive gas supply system 40. A downstream end of the supply system 40 forms an additive gas supply port (a plurality of ejection holes), which will be described below. The additive gas generator 18 and the supply system 40 constitute an exhaust gas processing mechanism. The configurations of these components will be specifically described below.

The static magnetic field generator 10 is composed of, for example, a superconducting magnet, and generates a static magnetic field. A sample is placed at the center of the magnetic field. In the illustrated example, the static magnetic field generator 10 has a bore 12 serving as a circular passage that pierces in the vertical direction.

The NMR probe 14 includes an insertion portion 22 that is inserted into the bore 12, and a base portion 20 that is contiguous with the insertion portion 22. The insertion portion 22 is inserted into the bore 12 through a lower opening of the bore 12. The base portion 20 is located below the static magnetic field generator 10.

An upper end portion of the insertion portion of the NMR probe 14 is a probe head 24. The probe head 24 has a head container (hereinafter simply referred to as "container") 25 which is a portion of a probe container. The container 25 is a hollow component, in which a structure body or a rotating mechanism 26 serving as a spinner is disposed. The rotating mechanism 26 is a mechanism for rotating a sample tube 28 containing a sample at a high speed while the sample tube 28 is being tilted at a predetermined angle (a magic angle). An internal space of the probe head 24 is separated from an internal space of the insertion portion main body by a separating wall 27.

The rotating mechanism 26 has a housing in which a sample chamber is present in the form of a cavity. The sample chamber houses a main portion of the sample tube therein, and a detection coil is disposed to surround the main portion of the sample tube. In the rotating mechanism 26, the sample tube is held by means of a plurality of air bearings while being kept out of contact with the housing. By blowing a jet stream (air) toward a turbine that is attached to the sample tube, the sample tube is driven to rotate. A VT gas (a sample temperature varying gas) is introduced into the sample chamber. In the illustrated embodiment, the VT gas has a temperature selected from a temperature range of, for example, −100° C. to +200° C. In the illustrated embodiment, as the exhaust gas processing mechanism for moderating the exhaust temperature (to make it closer to room temperature) is incorporated, the temperature range for the VT gas is substantially wider than a conventional temperature range. In other words, a VT gas having a lower temperature or a VT gas having a higher temperature can be used. This means that a sample can be measured under temperatures at which measurements would heretofore have been impractical.

Three pipes are connected to the rotating mechanism 26. Specifically, a VT gas pipe, a bearing gas pipe (not shown), and a drive gas pipe (not shown) are connected to the rotating mechanism 26. Referring to FIG. 1, the VT gas pipe is labeled with reference numerals 30a and 30b. Reference numeral 30a represents a pipe connecting between the base portion 20 and the VT gas generator 16. Reference numeral 30b represents a pipe disposed within the NMR probe 14. An optional heater 32 may be disposed at a midpoint of the pipe. The VT gas generator 16 includes, for example, a pump, a gas cooling unit, a gas heating unit, a flowmeter, and a flow rate controller. As the heater 32 serves as the gas heating unit, the heater 32, if disposed, forms, in effect, a portion of the VT gas generator 16. The VT gas includes, for example, air and nitrogen gas. FIG. 1 illustrates two ports formed on the base portion 20; that is, a port 34 through which a bearing gas is introduced, and a port 36 through which a drive gas is introduced.

Next, the exhaust gas processing mechanism will be described in detail. As described above, the exhaust gas processing mechanism includes, for example, the additive gas generator 18 and the supply system 40. The exhaust gas processing mechanism feeds an additive gas that is at room temperature (ordinary temperature) into the probe head 24 and mixes the additive gas with a high-temperature or low-temperature exhaust gas to moderate the exhaust temperature. The exhaust gas processing mechanism may also be referred to as "gas mixing mechanism."

The additive gas generator 18 includes, for example, a pump, a flowmeter, and a flow rate controller. In addition, a gas heating unit and a gas cooling unit may also be disposed. In other words, an additive gas having a temperature other than room temperature may be used to more effectively control the exhaust temperature. Typical NMR measurement systems include a compressor that generates compressed air. The additive gas generator 18 may be composed of such a compressor. In a preferred embodiment, a dryer for drying the additive gas to produce dry gas (dry air) is disposed in the additive gas generator 18.

The supply system 40 is a mechanism that supplies the additive gas to the probe head 24. The supply system 40 includes a pipe 42 and a pipe 43. The pipe 42 is disposed between a pipe structure located in the bore 12 and the additive gas generator 18, and the pipe 43 constitutes a portion of the pipe structure inserted in the bore 12. The pipe structure is a mechanical assembly or unit having a plurality of flow paths. Referring to the conceptual diagram in FIG. 1, the pipe structure includes an inner pipe 38 and an outer pipe 43 that are disposed so as to share the same center axis. In the pipe structure, an exhaust flow path 41 and an additive gas flow path 46 are formed in this manner. An outlet of the flow path 46 constitutes an additive gas ejection portion 44. In the illustrated embodiment, the additive gas ejection portion 44 is composed of, for example, four ejection holes. The additive gas ejection portion 44 forms a portion of the supply system 40.

A VT gas is continuously supplied to the rotating mechanism 26. The VT gas enters the sample chamber in the rotating mechanism 26, exchanges heat with the sample tube (and the sample), and then, is discharged from a discharge port via a discharge path that is in communication with the sample chamber. In other words, an exhaust gas is released into the probe head 24. Meanwhile, an additive gas is continuously supplied into the probe head 24. In the probe head 24, an additive gas (which may be at room temperature) exiting from the additive gas ejection portion 44 is mixed with an exhaust gas (which may be at a high temperature or at a low temperature) exiting from the rotating mechanism 26. An exhaust gas mixture is generated in this manner. The temperature of the exhaust gas mixture is closer to room temperature than is the temperature of the VT gas. Although, in the illustrated embodiment, air having room temperature is used as the additive gas, an additive gas having a temperature that is higher than room temperature may be used when the VT gas is at a temperature that is lower than room temperature, and an additive gas having a temperature that is lower than room temperature may be used when the VT gas is at a temperature that is higher than room temperature. In a preferred embodiment, the flow rate of the additive gas is controlled in accordance with the temperature and the flow rate of the VT gas. The exhaust gas mixture generated by mixing of the gases is released to the outside via the flow path 41. As described above, the method for processing an exhaust gas according to the illustrated embodiment includes two steps: a first step of supplying the VT gas to the sample chamber, and a second step of mixing the additive gas with the exhaust gas released from the sample chamber.

Although, in the configuration in FIG. 1, the additive gas is supplied to the probe head 24 via an upper opening of the bore 12, the additive gas may be supplied to the probe head 24 via the NMR probe 14, or, in other words, via the lower opening of the bore 12.

While, in conventional configurations, a container having a vacuum double glass pipe structure or a container having a water-cooled jacket structure has been used for thermal protection of structural elements located within or outside the probe head 24 from the exhaust gas, the above-described configuration eliminates the necessity to use such a special structure. However, for example, to further broaden the temperature variable range of the VT gas, the above-described gas mixing method may be used in combination with such a special structure.

Figure 2:
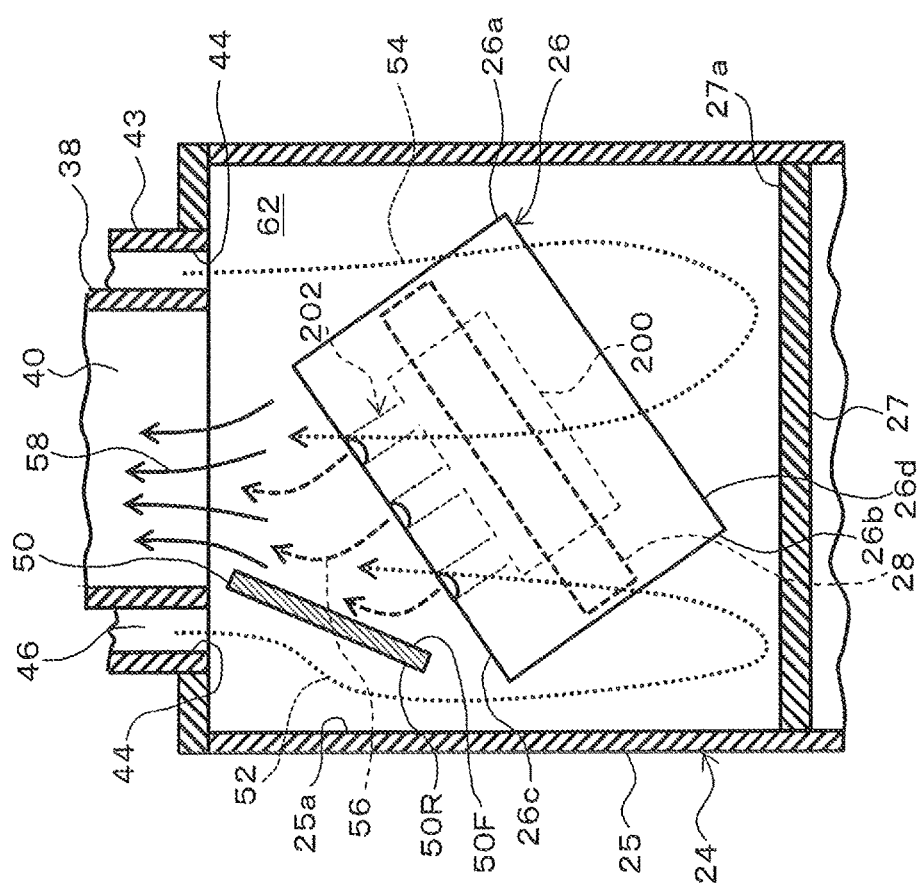
FIG. 2 is a cross-sectional view for illustrating mixing of gases in a probe head.

FIG. 2 illustrates an enlarged cross-sectional view of the probe head 24 illustrated in FIG. 1. In FIG. 2, for example, components and flows of gases are schematically illustrated for ease of understanding of the gas mixing function.

The rotating mechanism 26 is disposed in an internal space 62 of the probe head 24 in the manner as described above. The rotating mechanism 26 is a structure body that is separate from the container 25, and is held in the container 25 by means of a supporting component, which is not illustrated. The rotating mechanism 26 overall has a block or cylindrical shape having a center axis that coincides with the rotational axis of the sample tube 28. The center axis is tilted at a predetermined angle. In the configuration in FIG. 2, two sides 26a and 26b that are orthogonal to the center axis are sloped. Specifically, the side 26a faces diagonally upward, and the side 26b faces diagonally downward. An upper surface 26c is in the form of, for example, a flat surface or a cylindrical surface, and is a slope that faces diagonally upward. A lower surface 26d is in the form of, for example, a flat surface or a cylindrical surface, and is a slope that faces diagonally downward. A gap of a certain size is present around the rotating mechanism 26. In other words, the rotating mechanism 26 is disposed so as to be spaced apart from the inner wall surface of the container 25. The separating wall 27 serves as a base that supports the rotating mechanism 26, and also serves as a partition that encloses the internal space 62 on the bottom side (on the lower side in FIG. 2).

The rotating mechanism 26 has a sample chamber 200 that is in the form of a cavity in which the main portion (that is, the portion in which a sample is placed) of the sample tube 28 is housed. A VT gas supply port, which is not illustrated, is connected to the sample chamber 200. The VT gas pipe is connected to an inlet of the supply port. The inlet is disposed on the top, on the bottom, or on a side of the housing of the rotating mechanism 26. In a preferred embodiment, the position of the inlet of the supply port and the piping arrangement of the VT gas pipe are determined in a manner such that the VT gas pipe will not unnecessarily interfere with the flows of the gases in the container 25.

The sample chamber 200 serves as a gas reservoir, to which a VT gas is continuously supplied. As a result, the VT gas fills up the sample chamber 200. The VT gas and the sample tube 28 (in effect, the sample) exchange heat with each other, so that the sample is heated or cooled to a predetermined temperature. It should be understood that the VT gas is not used when the sample is measured at room temperature. A plurality of exhaust ports (a plurality of exhaust paths) are connected to the sample chamber 200, and the VT gas, or, in other words, the exhaust gas is discharged to the internal space 62 through a plurality of openings 202 at which the exhaust ports (the exhaust paths) terminate. The plurality of openings 202 collectively serve as a discharge port of the exhaust gas.

In the example in FIG. 2, the exhaust gas is discharged through the plurality of openings 202 in a direction orthogonal to the center axis of the rotating mechanism 26, that is, in a diagonally upward direction, toward a corner portion 25a which is a portion of the container 25. A deflector 50, which will be described in detail below, is disposed between the plurality of openings 202 and the corner portion 25a.

The pipe structure is disposed above the probe head 24. In the example in FIG. 2, the pipe structure includes the inner pipe 38 and the outer pipe 43. In other words, a coaxial double pipe structure is used. The inside of the pipe 38 is the exhaust flow path 41, through which an exhaust gas mixture flows. In the flow path 41, the side closer to the probe head 24 is the upstream side, and the side farther from the probe head 24 is the downstream side. A flow path located between the pipe 38 and the pipe 43 is the flow path 46. An additive gas is supplied to the internal space 62 of the probe head 24 via the flow path 46. In the illustrated example, the outlet of the flow path 46 forms a plurality of ejection holes (an additive gas ejection portion) 44. The additive gas is released vertically downward to the internal space 62 through the plurality of ejection holes 44.

Referring to FIG. 2, a major portion of the additive gas released to one side of the internal space 62 (where one of two ends of the rotating mechanism 26 that is lower than the other is located) flows through a gap between a rear surface 50R of the deflector 50 and the inner wall surface of the container 25, and then flows toward a bottom surface 27a through a gap around the rotating mechanism 26. The additive gas bounced back by the function of the bottom surface 27a flows around the rotating mechanism 26 to above the rotating mechanism 26, in particular, toward a front surface 50F of the deflector. The overall flow described above is indicated by reference numeral 52. On the other hand, a major portion of the additive gas released to another side of the internal space 62 (where one of two ends of the rotating mechanism 26 that is higher than the other is located) flows downward along the inner wall surface of the container 25, and then flows toward the bottom surface 27a through a gap around the rotating mechanism 26. The additive gas bounced back by the function of the bottom surface 27a flows around the rotating mechanism 26 to above the rotating mechanism 26. The overall flow described above is indicated by reference numeral 54.

A major portion of an exhaust gas 56 exiting through the three openings 202 that constitute the discharge port is captured by the deflector and is guided toward the flow path 41. The remaining portion also flows toward the flow path 41. The additive gas 52 and 54 that, at that time, has come up from below the rotating mechanism 26 around the rotating mechanism 26 is mixed with the exhaust gas 56 to produce an exhaust gas mixture 58. As the exhaust gas 56 has a predetermined temperature that is, for example, a high temperature or a low temperature, and as the additive gas 52 and 54 is of room temperature, the mixing of these gases moderates the temperature of the exhaust gas 56 from the predetermined temperature toward room temperature. In other words, the exhaust gas mixture 58 that is thermally moderated is produced. As a result, components located within or outside the probe head, in particular, thermally weak components, can be protected from becoming too hot or too cold.

Although typical flows are described above, actual flows of gases in the internal space 62 are complex. In a preferred embodiment, the positions and the orientation of the plurality of ejection holes 44 are optimized and, additionally, the position and the shape of the deflector 50 are optimized through, for example, simulations or experiments so that, in any case, the additive gas exiting through the plurality of ejection holes 44 does not directly collide with the exhaust gas 56 exiting through the plurality of openings 202, in other words, so that the flow paths of the additive gas 52 and 54 smoothly merge with the flow paths of the exhaust gas 56. Although, in the above-described embodiment, the mixing of the gases is performed in the probe head 24, the mixing of the gases may be either partially or entirely performed in the pipe 38. It should be understood that, in actual implementation, a temperature gradient is formed from the internal space 62 of the probe head 24 to the flow path 41.

In the configuration in FIG. 2, the exhaust gas is captured and guided by the front surface 50F of the deflector 50 and, in other words, the exhaust gas 56 is prevented from being blown directly against the corner portion 25a. This can prevent or moderate problems associated with a rise or a drop in temperature of the corner portion 25a. Particularly, because the additive gas having room temperature flows between the corner portion 25a and the rear surface 50R of the deflector 50, a temperature change of the corner portion 25a is effectively retarded.

While some of the bearing gas or the drive gas may flow into the sample chamber 200 in the rotating mechanism 26, the amount of the gas that flows in is slight in most cases. While some of those gases may be released to the internal space 62, because the amount of such a gas is slight in most cases, the gas does not significantly change the temperature of the exhaust gas. The flow rate A (l/min) of the additive gas is determined in accordance with the flow rate B (l/min) of the exhaust gas. In the illustrated embodiment, the flow rate A is greater than the flow rate B.

Figure 3:
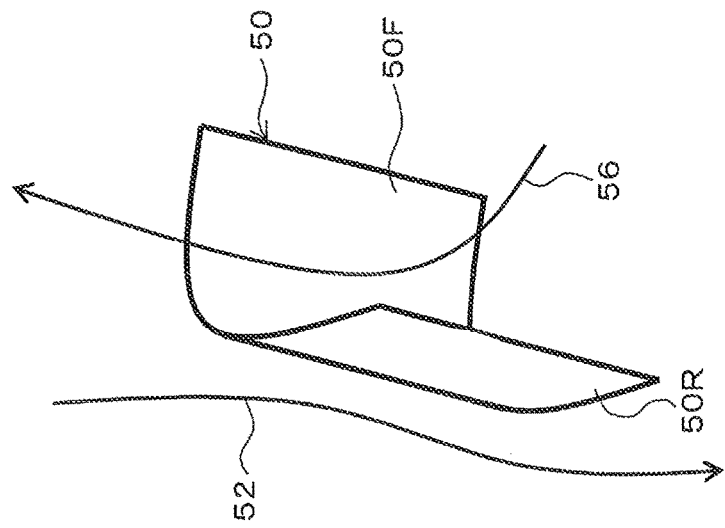
FIG. 3 is a perspective view illustrating a deflector.

FIG. 3 illustrates a shape of the deflector 50 in the form of a perspective view. The front surface 50F of the deflector 50 has a concave curved shape. This shape enhances the function of capturing and guiding the exhaust gas 56. In a preferred embodiment, the shape of the deflector 50 is determined in accordance with the conditions under which the exhaust gas is exhausted. In the example in FIG. 3, the rear surface 50R of the deflector 50 has a convex curved shape. With this shape, the flow of the additive gas 52 can be smoothly divided to both sides of the rotating mechanism. It should be understood that the configuration illustrated in FIG. 3 is given only by way of example.

A first embodiment and a second embodiment that are specific examples of the above-described exhaust gas processing mechanism will be described below.

Figure 5:
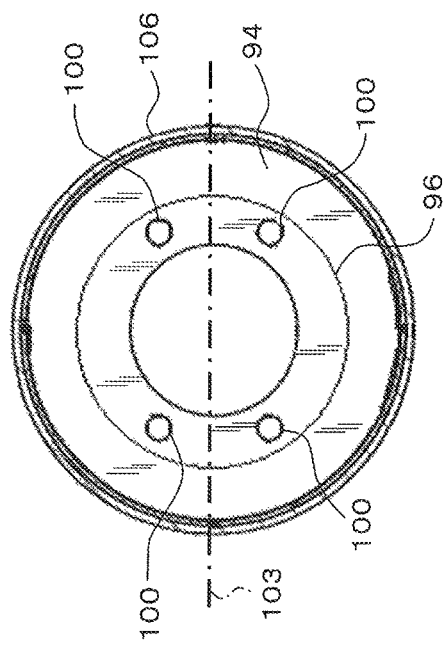
FIG. 5 is a cross-sectional view illustrating a cross section A-A.
Figure 4:
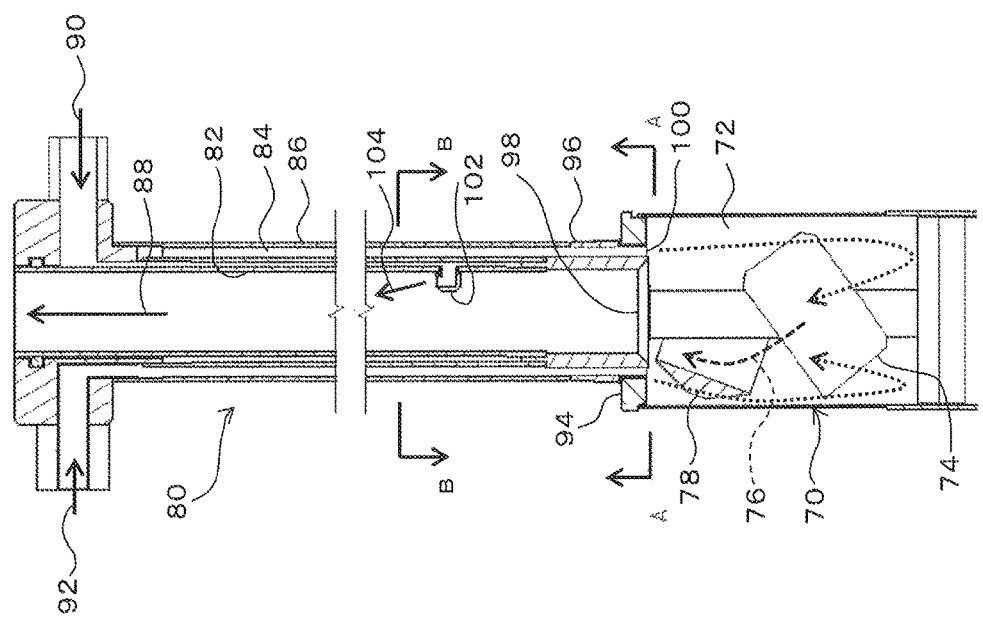
FIG. 4 is a cross-sectional view illustrating a first embodiment.
Figure 6:
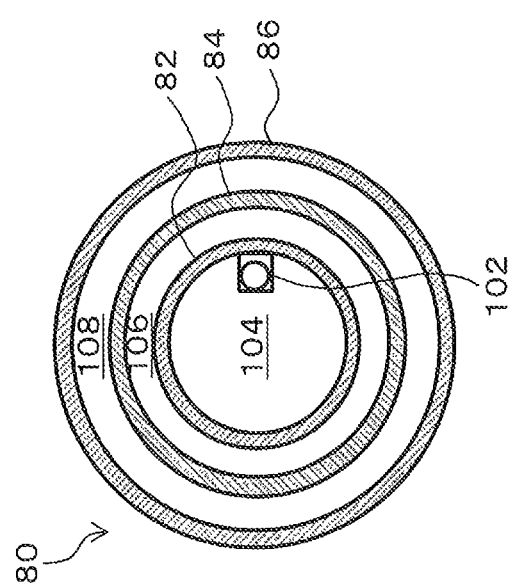
FIG. 6 is a cross-sectional view illustrating a cross section B-B.

FIGS. 4 to 6 illustrate an exhaust gas processing mechanism according to the first embodiment. These figures do not illustrate a source from which the additive gas is supplied. A rotating mechanism 74 is disposed in an internal space 72 of a probe head 70. A deflector 78 is disposed diagonally above the rotating mechanism 74 (in a direction toward which an exhaust gas 76 exiting through an exhaust outlet is moving). The deflector 78 has a curved shape as described above.

A disk- or ring-shaped plate 94 is disposed above the probe head 70. In the illustrated example, the plate 94 constitutes a portion of a container of the probe head 70. A pipe structure 80 is connected to the probe head 70 via a joint component 96. In the illustrated example, the joint component 96 also is a component of the probe. The joint component 96 may constitute a portion of the pipe structure 80. The joint component 96 has four ejection holes 100 that face the internal space 72. The arrangement of the ejection holes 100 will be described below with reference to FIG. 5. The additive gas rushes into the internal space 72 through the four ejection holes 100. Reference numeral 98 represents an exhaust outlet.

The pipe structure 80 disposed above the probe has, in this example, a coaxial triple pipe structure. Specifically, the pipe structure 80 includes a first pipe (an inner pipe) 82, a second pipe (a middle pipe) 84, and a third pipe (an outer pipe) 86. A space between the second pipe 84 and the third pipe 86 is a flow path in which an additive gas 92 flows. The inside of the first pipe 82 is a flow path in which an exhaust gas mixture (a thermally processed exhaust gas) 88 flows. A space between the first pipe 82 and the second pipe 84 is a flow path in which a shield gas 90 is fed. A shield gas layer (a thermal insulation layer) formed between the flow path for the exhaust gas mixture and the flow path for the additive gas can reduce the heat exchange between these two flow paths (between two gases), and can, in particular, prevent the weakening of the gas mixing function due to the cooling or heating of the additive gas. The shield gas is, for example, air or nitrogen gas of room temperature. To obtain an improved thermal insulation function, the temperature of the shield gas may be varied.

In the first embodiment, an ejection portion 102 that ejects the shield gas to the exhaust gas flow path is disposed. The ejection portion 102 rushes the shield gas toward the downstream side of the exhaust gas mixture flow path. As the velocity of the flow of the exhaust gas mixture is increased in this manner, the gas pressure lowers on the side upstream of the ejection portion 102, which promotes the exhaust from the probe head 70. A plurality of ejection portions may be disposed. A similar effect may be obtained by ejecting a different gas rather than the shield gas. Also, suction may be performed on the downstream side of the exhaust gas mixture flow path. Referring to FIG. 4, a T-shaped joint portion that constitutes an upper portion of the pipe structure 80 is disposed outside the bore.

FIG. 5 illustrates a cross section taken at the position A-A in FIG. 4. The plate 94, which is shaped in a ring, and the joint component 96, which is also shaped in a ring, appear in this cross section. Alternate long and short dashed lines 103 correspond to the center axis (the rotational axis) of the rotating mechanism and are a projection of the center axis on the cross section. For example, a first end portion of the rotating mechanism that is located on the left side as seen in FIG. 5 is lower than a second end portion of the rotating mechanism that is located on the right side as seen in FIG. 5, and the second end portion of the rotating mechanism is higher than the first end portion of the rotating mechanism. Two ejection holes 100 are disposed to eject the additive gas toward both sides of the first end portion (both upward and downward as seen in FIG. 5) across the center line. Similarly, two ejection holes 100 are disposed to eject the additive gas toward both sides of the second end portion across the center line. With this layout of the ejection holes, appropriate flow paths for the additive gas can be formed in the probe head. It should be understood that the layout illustrated in FIG. 5 is given only by way of example, and other layouts of the ejection holes may be adopted depending on, for example, the structure within the probe head.

FIG. 6 illustrates a cross section taken at the position B-B in FIG. 4. FIG. 6 is a schematic diagram for ease of understanding of the structure; for example, the diameters of individual pipes are not necessarily accurate. As described above, the pipe structure 80 includes the three pipes 82, 84, and 86 that are disposed concentrically. Reference numeral 104 represents a flow path for the exhaust gas mixture, reference numeral 106 represents a flow path (a reservoir layer) for the shield gas, and reference numeral 108 represents a flow path for the additive gas. The ejection portion 102 is disposed so as to protrude into the flow path 104.

Figure 7:
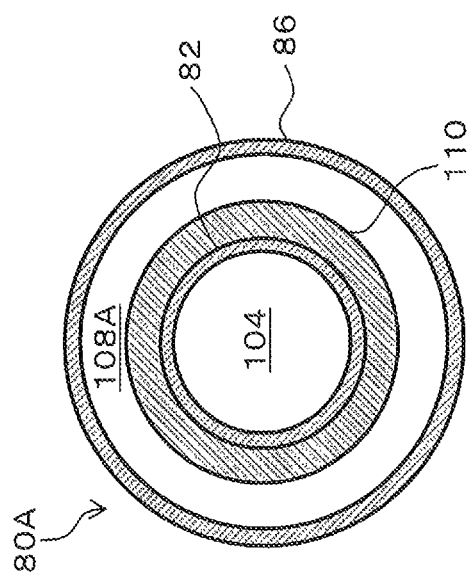
FIG. 7 illustrates a modification example.

FIG. 7 illustrates a modification example. A pipe structure 80A includes two pipes 82 and 86 that are disposed concentrically. Reference numeral 104 represents a flow path for the exhaust gas mixture, and reference numeral 108A represents a flow path for the additive gas. A thermal insulation material 110 is disposed between these flow paths 104 and 108A. The thermal insulation material 110 has a hollow cylindrical shape having a center axis that coincides with the center axis of, for example, the pipe 82. In the example in FIG. 7, the thermal insulation material 110 is disposed so as to serve as an outer sheath for the pipe 82. A thermal insulation material may also be disposed inside the pipe 82. Further, a vacuum double pipe structure may also be used.

Figure 8:
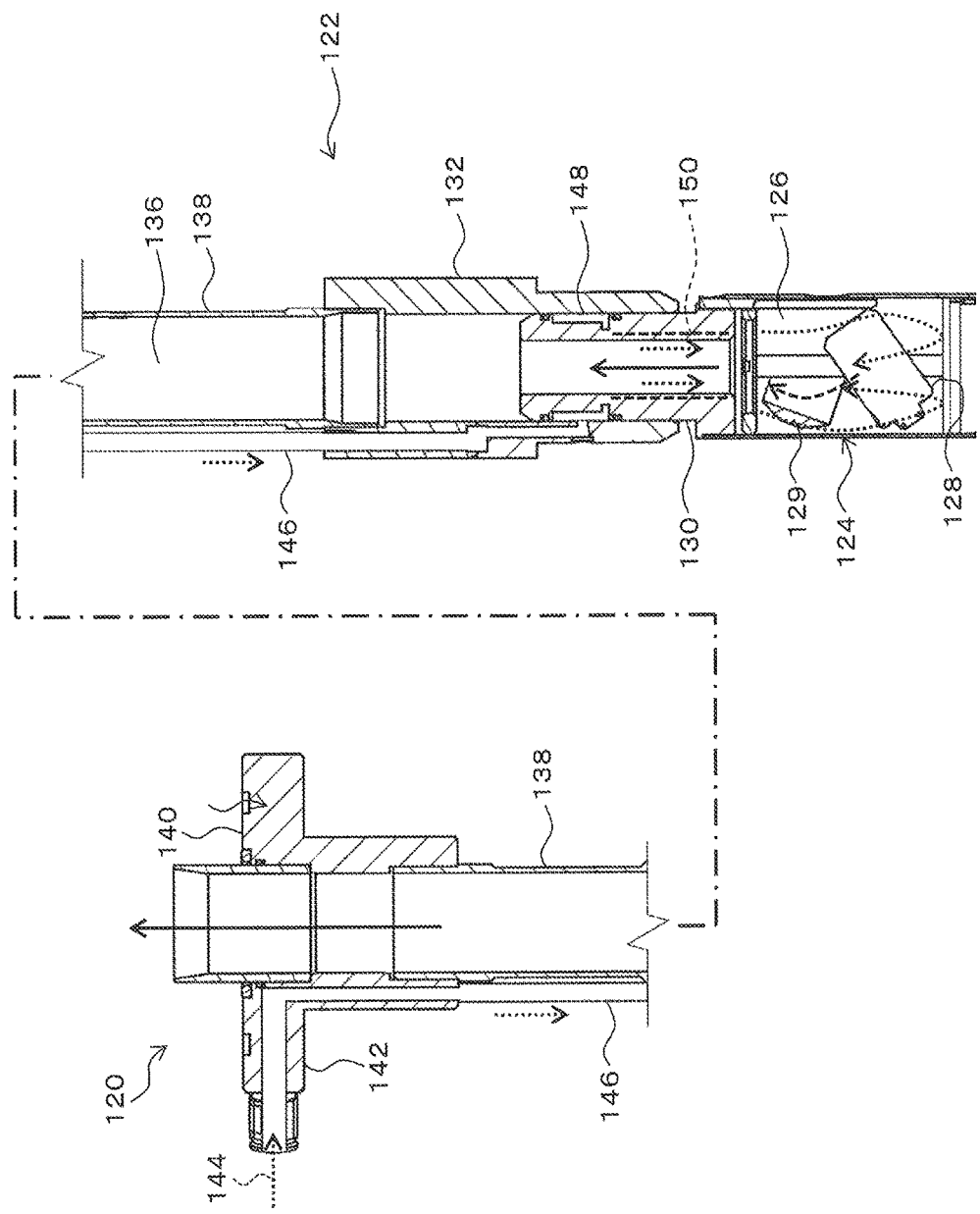
FIG. 8 is a cross-sectional view illustrating a second embodiment.
Figure 9:
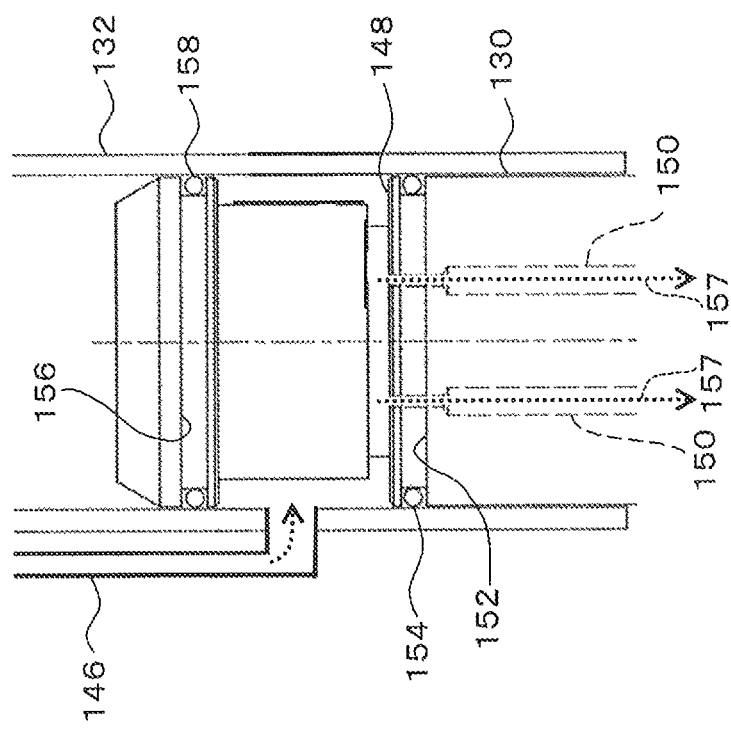
FIG. 9 is a diagram for illustrating flow paths for an additive gas.

FIGS. 8 and 9 illustrate an exhaust gas processing mechanism according to the second embodiment. These figures for the second embodiment also do not illustrate a source from which the additive gas is supplied. The structure of the second embodiment is simpler than that of the first embodiment, and the second embodiment is more suited for practical use. In FIG. 8, the left side illustrates an upper portion 120 of the pipe structure, and the right side illustrates a middle portion and a lower portion 122 of the pipe structure. The right side also illustrates a probe head 124.

A rotating mechanism 128 is disposed in an internal space 126 of the probe head 124. A deflector 129 is disposed diagonally above the rotating mechanism 128 (in a direction toward which an exhaust gas exiting through an exhaust outlet is moving). The deflector 129 has a curved shape.

The pipe structure is connected above the probe head 124 via a first joint component 130 and a second joint component 132 which are hollow components. In the illustrated example, the first joint component 130 constitutes a component of the probe. Alternatively, the first joint component 130 may constitute a component that is located outside the probe. The second joint component 132 is connected, in this example, below the pipe structure. The second joint component 132 may be taken as a portion of the pipe structure.

The first joint component 130 has a hollow tubular portion that projects upward. The second joint component 132 has a hollow shape. The tubular portion of the first joint component 130 is inserted into an opening of the second joint component 132. The pipe structure is connected to the probe with the first joint component 130 and the second joint component 132 being kept in the inserted state. Two O rings or seal components spaced apart from each other in the vertical direction are disposed on an outer surface of the tubular portion. The O rings or the seal components provide a sealing function under the above-described inserted state.

The first joint component 130 has an annular recess 148 that forms a gap into which the additive gas is fed, and four through holes 150 that extend in the vertical direction are in communication with the gap. The four through holes 150 have outlets that face the internal space 126 and form four ejection holes. The layout of the ejection holes is similar to that illustrated in FIG. 5.

The pipe structure includes a pipe 138 that forms an exhaust flow path 136, and a pipe 146 disposed outside the pipe 138. The inside of the pipe 146 is a flow path in which the additive gas flows. A port 142 is connected to an upper end of the pipe 146. An additive gas 144 is fed into the port 142 through another pipe. A third joint component 140 is disposed on the downstream side of the exhaust flow path 136, or, in other words, at an upper end of the pipe 138. The third joint component 140 and the port 142 are located outside the bore.

FIG. 9 is a schematic diagram illustrating the connection of the two joint components 130 and 132. The first joint component 130 has a tubular portion that projects upward, and two ring grooves 152 and 156 spaced apart from each other in the vertical direction are formed in an upper end portion of the tubular portion. Two O rings 154 and 158 are housed in the ring grooves 152 and 156. The additive gas is fed into a gap defined by the annular recess 148 via the pipe 146. The four through holes 150 are in communication with the gap, and an additive gas 157 is fed into the probe head via the four through holes 150. As the upper side and the lower side of this gap space are hermetically sealed by the two O rings 154 and 158, the additive gas will not leak from the sealed space.

In the second embodiment, because it is not necessary to adopt a coaxial multiple pipe structure, the configuration can be simplified. Additionally, the connection of the two joint components 130 and 132 provides an advantage in that the additive gas flow path can be formed easily. More specifically, the additive gas flow path and the exhaust gas flow path can be formed easily by fitting, from above the bore, the pipe structure including the second joint component 132 on the probe including the first joint component 130, which is inserted through the lower opening in the bore.

In the exhaust gas processing mechanism based on the mixing of the gases, the exhaust gas mixture can be generated by mixing the additive gas with the exhaust gas in the internal space of the probe head. In other words, a thermally processed exhaust gas can be generated. Additionally, as a deflector is used for directing the flow of the exhaust gas, thermal damage to structural elements (such as a shim coil, a resin, an elastic member, or an adhesive) located within the probe can be effectively avoided. Another advantage is that the temperature variable range of the VT gas can be broadened. For example, the temperature of the VT gas can be varied over a wider range of from −100° C. to +200° C. This means that the sample temperature during the nuclear magnetic resonance measurement can be controlled over a wider range. More specifically, the above-described exhaust gas processing mechanism makes it possible to observe material states that were not observable by conventional apparatuses.

Figure 10:
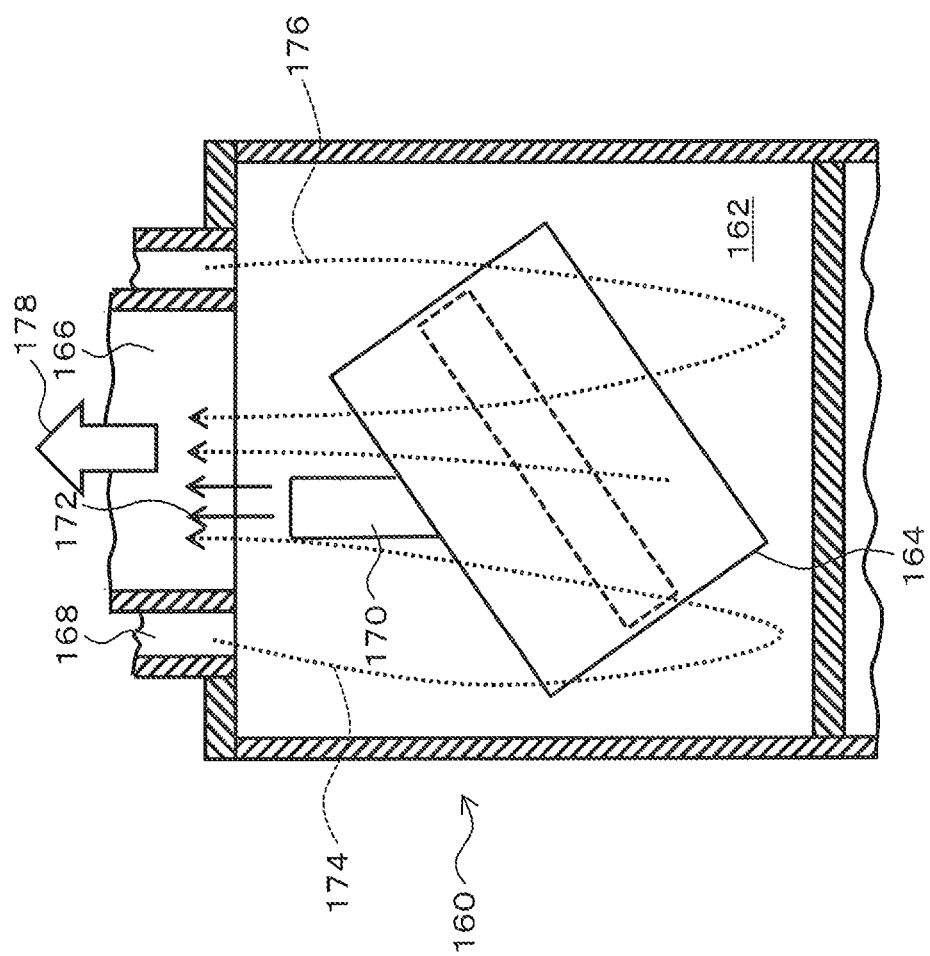
FIG. 10 illustrates a rotating mechanism having a projecting exhaust port.

FIG. 10 illustrates a modification example of the rotating mechanism. A rotating mechanism 164 is disposed in an internal space 162 of a probe head 160. While the rotating mechanism 164 has a structure basically the same as that of the rotating mechanisms described above, the rotating mechanism 164 includes an exhaust port 170 that projects upward like a chimney. The exhaust port 170 has an outlet serving as a discharge opening through which an exhaust gas 172 is exhausted. An additive gas 174 and 176 fed into the internal space 162 through an additive gas flow path 168 circulates within the internal space, and is then mixed with the exhaust gas 172. An exhaust gas mixture 178 is produced in this manner. The temperature of the exhaust gas mixture 178 is closer to room temperature than is the temperature of the VT gas that is fed into the rotating mechanism 164.

Although the configuration in FIG. 10 does not include a deflector, the direction of the flow of the exhaust gas 172 can be defined by the exhaust port 170. Specifically, the exhaust gas is discharged toward the downstream side of the exhaust path. The additive gas is mixed at a midpoint of the flow path. The mixing area extends from within the probe head 160 to a lower portion of the pipe structure (including a joint component that is a hollow component). The configuration in FIG. 10 also can prevent structural elements located within the probe head from becoming too hot or too cold. The flow of the additive gas basically does not collide against the flow of the exhaust gas, and the flow paths of the two gases merge smoothly; therefore, it can be expected that the gases are mixed smoothly while being prevented from staying in the same place. In a preferred embodiment, flows of individual gases are formed so as to prevent the exhaust gas mixture or the exhaust gas that has not been mixed, from returning to the internal space 162 or from staying in the same place in the internal space 162.

The above-described exhaust gas processing mechanism based on the mixing of the gases may be generally applied to nuclear magnetic resonance measurement apparatuses in which a VT gas is used. It should be noted that, because, in a nuclear magnetic resonance measurement apparatus that measures solid samples, the exhaust gas from the rotating mechanism is discharged into the probe head and often thermally influences components located within or outside the probe head, it is advantageous to incorporate the above-described exhaust gas processing mechanism in such an apparatus.

The invention claimed is:

1. A nuclear magnetic resonance measurement apparatus comprising:
a structure body having a sample space, the space being configured to house a sample that is to be measured by nuclear magnetic resonance, into which a sample gas for adjusting a temperature of the sample to a predetermined temperature is introduced;
a container of a nuclear magnetic resonance measurement probe configured to house the structure body; and
an exhaust gas processing mechanism comprising an additive gas generator for generating an additive gas and an additive gas pipe provided between the additive gas generator and the container and configured to feed the additive gas into the container,
wherein the exhaust gas processing mechanism is configured to mix the additive gas with an exhaust gas that is the sample gas exiting from the sample space, to generate an exhaust gas mixture having a temperature that is closer to room temperature than is the predetermined temperature.

2. The nuclear magnetic resonance measurement apparatus according to claim 1,
wherein the structure body has a discharge port configured to discharge the exhaust gas into the container, and
wherein in the container, the additive gas is mixed with the exhaust gas discharged through the discharge port.

3. The nuclear magnetic resonance measurement apparatus according to claim 2, wherein the structure body is a rotating mechanism configured to rotate a sample tube in which the sample is placed.

4. The nuclear magnetic resonance measurement apparatus according to claim 3,
wherein a first pipe configured to feed the sample gas and a second pipe configured to feed a gas for rotating the sample tube are connected to the rotating mechanism, and
wherein the additive gas pipe is different from the first pipe and the second pipe.

5. The nuclear magnetic resonance measurement apparatus according to claim 4, wherein the exhaust gas processing mechanism includes at least one ejection hole that is in communication with the additive gas pipe, the at least one ejection hole being configured to eject the additive gas into the container.

6. The nuclear magnetic resonance measurement apparatus according to claim 5, wherein the exhaust gas processing mechanism includes a plurality of ejection holes configured to eject the additive gas toward a periphery of the rotating mechanism.

7. The nuclear magnetic resonance measurement apparatus according to claim 6, wherein in the container, a flow of the additive gas extending from the plurality of ejection holes merges with a flow of the exhaust gas extending from the discharge port.

8. The nuclear magnetic resonance measurement apparatus according to claim 2,
wherein a deflector is disposed in the container, and
wherein the exhaust gas exiting through the discharge port is guided by the deflector toward an exhaust outlet.

9. The nuclear magnetic resonance measurement apparatus according to claim 8, wherein a flow of the exhaust gas and a flow of the additive gas are separated by the deflector.

10. The nuclear magnetic resonance measurement apparatus according to claim 8, wherein the deflector has a surface that faces toward the discharge port, the surface being a concave curved surface.

11. The nuclear magnetic resonance measurement apparatus according to claim 2,
wherein the structure body has an exhaust port that projects in a direction toward which the exhaust gas mixture flows, and
wherein an end of the exhaust port is the discharge port.

12. The nuclear magnetic resonance measurement apparatus according to claim 3, comprising a pipe structure including the additive gas pipe connected to the container, the pipe structure comprising:
a first flow path in which the exhaust gas mixture flows;
a second flow path defined by the additive gas pipe in which the additive gas flows; and
a third flow path in which a shield gas flows, the third flow path being disposed between the first flow path and the second flow path to prevent or reduce heat exchange between the exhaust gas mixture and the additive gas.

13. The nuclear magnetic resonance measurement apparatus according to claim 12, wherein the pipe structure includes a shield gas ejection hole configured to feed the shield gas into the first flow path toward the downstream side of the first flow path.

14. A method for processing an exhaust gas in a nuclear magnetic resonance measurement apparatus, the method comprising:
introducing a sample gas for heating or cooling a sample that is to be measured by nuclear magnetic resonance, into a sample space that houses the sample to adjust a temperature of the sample to a predetermined temperature, the sample space defined by a structure body housed within a container of a nuclear magnetic resonance measurement probe;
feeding an additive gas into the container via an additive gas pipe provided between an additive gas generator and the container;
mixing the additive gas with an exhaust gas that is the sample gas exiting from the sample space, to generate an exhaust gas mixture having a temperature that is closer to room temperature than is the predetermined temperature; and
exhausting the exhaust gas mixture.

* * * * *